United States Patent
Kapadia et al.

(10) Patent No.: US 11,219,494 B2
(45) Date of Patent: *Jan. 11, 2022

(54) ROBOTIC SURGICAL ASSEMBLIES

(71) Applicant: Covidien LP, Mansfield, MA (US)

(72) Inventors: Jaimeen Kapadia, Cambridge, MA (US); Josiah Rosmarin, Sebring, FL (US)

(73) Assignee: Covidien LP, Mansfield, MA (US)

( * ) Notice: Subject to any disclaimer, the term of this patent is extended or adjusted under 35 U.S.C. 154(b) by 58 days.

This patent is subject to a terminal disclaimer.

(21) Appl. No.: 16/815,150

(22) Filed: Mar. 11, 2020

(65) Prior Publication Data

US 2020/0205915 A1 Jul. 2, 2020

Related U.S. Application Data

(63) Continuation of application No. 15/580,143, filed as application No. PCT/US2016/037821 on Jun. 16, 2016, now Pat. No. 10,595,945.

(Continued)

(51) Int. Cl.
*B25J 9/16* (2006.01)
*A61B 34/35* (2016.01)
(Continued)

(52) U.S. Cl.
CPC ........ *A61B 34/35* (2016.02); *A61B 17/00234* (2013.01); *A61B 34/30* (2016.02);
(Continued)

(58) Field of Classification Search
CPC ............. A61B 34/35; A61B 17/00; B25J 9/16
See application file for complete search history.

(56) References Cited

U.S. PATENT DOCUMENTS

| 5,810,880 A | 9/1998 | Jensen et al. |
| 6,923,613 B2 | 8/2005 | Stuyt |

(Continued)

FOREIGN PATENT DOCUMENTS

| JP | 2002500524 A | 1/2002 |
| JP | 2011224368 A | 11/2011 |

(Continued)

OTHER PUBLICATIONS

European Search Report dated Jan. 24, 2019, corresponding to counterpart European application No. 16812414.7; 10 pages.

(Continued)

*Primary Examiner* — Kira Nguyen

(57) ABSTRACT

A surgical assembly for use with and for selective connection to a robotic arm includes an electromechanical instrument and an instrument drive unit. The instrument drive unit includes a motor and a feedback assembly. The motor is configured to effect rotation of the electromechanical instrument. The feedback assembly includes control circuitry and first and second annular members. The control circuitry is configured to sense a change in a condition of the motor. The first annular member has a surface feature projecting therefrom. The second annular member is disposed adjacent the first annular member and has a first surface feature projecting therefrom, circumferentially aligned with the surface feature of the first annular member. Upon a threshold amount of rotation of the first annular member, the surface feature of the first annular member abuts the first surface feature of the second annular member to change the condition of the motor.

20 Claims, 6 Drawing Sheets

Related U.S. Application Data

(60) Provisional application No. 62/181,879, filed on Jun. 19, 2015.

(51) Int. Cl.
*A61B 34/30* (2016.01)
*A61B 17/00* (2006.01)
*A61B 90/00* (2016.01)
*A61B 34/00* (2016.01)

(52) U.S. Cl.
CPC ........... *B25J 9/1669* (2013.01); *B25J 9/1689* (2013.01); *A61B 34/74* (2016.02); *A61B 2017/00199* (2013.01); *A61B 2017/00314* (2013.01); *A61B 2017/00398* (2013.01); *A61B 2017/00477* (2013.01); *A61B 2090/035* (2016.02); *Y10S 901/09* (2013.01); *Y10S 901/23* (2013.01)

(56) References Cited

U.S. PATENT DOCUMENTS

| | | |
|---|---|---|
| 6,991,627 B2 | 1/2006 | Madhani et al. |
| 7,204,844 B2 | 4/2007 | Jensen et al. |
| 8,517,241 B2 | 8/2013 | Nicholas et al. |
| 8,828,023 B2 | 9/2014 | Neff et al. |
| 10,595,945 B2 | 3/2020 | Kapadia et al. |
| 10,806,526 B2 * | 10/2020 | Prindiville ............. A61B 17/29 |
| 2011/0015650 A1 | 1/2011 | Choi et al. |
| 2011/0277775 A1 | 11/2011 | Holop et al. |
| 2012/0116416 A1 | 5/2012 | Neff et al. |
| 2012/0199630 A1 | 8/2012 | Shelton, IV |
| 2013/0046317 A1 * | 2/2013 | Blumenkranz ........ A61B 34/70 606/130 |
| 2013/0046318 A1 * | 2/2013 | Radgowski ............ A61B 34/30 606/130 |
| 2013/0123783 A1 | 5/2013 | Marczyk et al. |
| 2013/0172713 A1 | 7/2013 | Kirschenman |
| 2013/0324998 A1 | 12/2013 | Kimball et al. |
| 2013/0325034 A1 | 12/2013 | Schena et al. |
| 2014/0207152 A1 * | 7/2014 | Fischvogt ............. A61B 17/068 606/139 |
| 2014/0263539 A1 | 9/2014 | Leimbach et al. |
| 2014/0309625 A1 * | 10/2014 | Okamoto ................ A61B 34/71 606/1 |
| 2015/0025538 A1 | 1/2015 | Kust et al. |

FOREIGN PATENT DOCUMENTS

| | | |
|---|---|---|
| JP | 2018522632 A | 8/2018 |
| WO | 2012104785 A1 | 8/2012 |
| WO | 2015023853 A1 | 2/2015 |

OTHER PUBLICATIONS

International Serach Report dated Jul. 9, 2015, corresponding to International Application No. PCT/US2015/026057; 5 pages.
International Serach Report dated Sep. 12, 2016, corresponding to International Application No. PCT/US2016/037821; 4 pages.
Chinese Office Action (with English translation), dated Apr. 27, 2020, corresponding to counterpart Chinese Application No. 201680035635.2; 19 total pages.
Japanese Office Action (with English translation) dated Mar. 16, 2020, corresponding to counterpart Japanese Application No. 2017-565156; 7 total pages.
Chinese Office Action dated Oct. 16, 2020, issued in corresponding Chinese Appln. No. 201680035635, 6 pages.
Japanese Office Action dated May 21, 2021, issued in corresponding Japanese Appln. No. 2020121125, 7 pages.
Indian Office Action dated Jan. 18, 2021, issued in corresponding Indian Appln. No. 201717045721, 6 pages.
Japanese Notice of Allowance with English Summary Form, dated Jun. 24, 2020, corresponding to counterpart Japanese Application No. 2017-565156; 4 total pages.

* cited by examiner

ROBOTIC SURGICAL ASSEMBLIES

CROSS-REFERENCE TO RELATED APPLICATION

This application is a continuation application of U.S. patent application Ser. No. 15/580,143, filed on Dec. 6, 2017, which is a national stage entry of International Patent Application No. PCT/US2016/037821, filed on Jun. 16, 2016, which claims the benefit of and priority to U.S. Provisional Application No. 62/181,879, filed on Jun. 19, 2015, the entire contents of each of which being incorporated by reference herein.

BACKGROUND

Robotic surgical systems have been used in minimally invasive medical procedures. Some robotic surgical systems include: a console supporting a surgical robotic arm, integrated motors having outputs actuating a surgical instrument coupled to a robotic arm of surgical system, and a surgical instrument having at least one end effector (e.g., forceps or a grasping tool). The surgical instrument included a rotatable shaft, the rotation of which was controlled by one of the integrated motors in the surgical system.

The integrated motors were located away from the part of the system where the surgical instrument was attached. This required a complex mechanical power transmission medium to apply the torque outputted by the integrated motors to inputs of the surgical instrument in order to actuate different components of the surgical instrument. Additionally, the integrated motors were difficult to service and repair as the surgical system had to be opened to gain access to the motors for servicing.

The rotatable shaft in the surgical instrument was prone to wear and limited the lifespan of the instrument. The additional components needed to enable shaft rotation also collected dirt and had to be cleaned to enable the surgical instrument to be reused.

There is a need for a surgical robotic system that is able to provide surgical instrument actuating motors that are easily interchangeable or serviceable. There is also a need for surgical robotic systems that can enable rotation of the surgical instrument end effectors while minimizing the need for additional components in the surgical instrument.

SUMMARY

In accordance with an aspect of the present disclosure, provided is a surgical assembly for use with and for selective connection to a robotic arm. The surgical assembly includes an electromechanical surgical instrument and an instrument drive unit. The surgical instrument includes a housing portion supporting a driven member therein, and a shaft having a proximal end supported by the housing portion and a distal end having an end effector operably coupled to the driven member. The instrument drive unit includes a first motor, a second motor, and a feedback assembly. The first motor is configured to be operably coupled to the driven member of the electromechanical surgical instrument. The second motor is configured to be coupled to the housing portion of the electromechanical surgical instrument to effect rotation of the electromechanical surgical instrument. The feedback assembly includes control circuitry, a first annular member, and a second annular member. The control circuitry is in communication with the second motor and configured to sense a change in a condition of the second motor. The first annular member has a surface feature projecting therefrom. The second annular member is disposed adjacent the first annular member. The second annular member has a first surface feature projecting therefrom circumferentially aligned with the surface feature of the first annular member such that upon a threshold amount of rotation of the first annular member, the surface feature of the first annular member abuts the first surface feature of the second annular member to change the condition of the second motor.

In some embodiments, the change in condition of the second motor may be a change in current delivered to the second motor upon the abutment of the surface feature of the first annular member and the first surface feature of the second annular member.

It is contemplated that the second annular member may have a second surface feature projecting therefrom, circumferentially spaced from the first surface feature. The instrument drive unit may further include an outer shell having a surface feature extending inwardly therefrom such that upon the second annular member achieving a threshold amount of rotation relative to the outer shell, the second surface feature of the second annular member abuts the surface feature of the outer shell to stop rotation of the electromechanical surgical instrument. The control circuitry may be configured to stop operation of the second motor upon the second surface feature of the second annular member abutting the surface feature of the outer shell.

It is envisioned that the instrument drive unit may further include an outer shell configured to be coupled to a robotic arm, and an inner hub rotatably disposed within the outer shell. The inner hub may be configured to be non-rotatably coupled to the housing portion of the electromechanical instrument. The second motor may include an outer stator, and an inner rotor. The outer stator may be fixedly coupled to the outer shell, and the inner rotor may be rotatably disposed within the outer stator. The inner rotor may have an inner surface that defines a longitudinal channel having the inner hub non-rotatably disposed therein. Actuation of the second motor may rotate the inner hub to effect rotation of the electromechanical instrument along a longitudinal axis thereof. The instrument drive unit may further include an outer hub disposed between the inner rotor and the inner hub such that the outer hub transmits rotational movement of the inner rotor to the inner hub. The instrument drive unit may further include an inner shell rotatably disposed within the outer shell. The inner shell may have a proximal end coupled to the inner hub and a distal end configured to be coupled to a proximal end of the electromechanical instrument such that the inner shell transmits rotational movement of the inner hub to the electromechanical instrument.

In some embodiments, the surgical assembly may further include a slider having a first portion configured to be movably connected to the robotic arm and a second portion defining an opening therethrough configured for receipt of the instrument drive unit.

In another aspect of the present disclosure, a robotic surgical system is provided and includes a surgical robotic arm, an electromechanical surgical instrument, and an instrument drive unit. The surgical instrument includes a housing portion supporting a driven member therein, and a shaft having a proximal end supported by the housing portion and a distal end having an end effector operably coupled to the driven member. The instrument drive unit includes a first motor, a second motor, and a feedback assembly. The first motor is configured to be operably coupled to the driven member of the electromechanical surgical instrument. The second motor is configured to be coupled to the housing portion of the electromechanical surgical instrument to effect rotation of the electromechanical surgical instrument. The feedback assembly includes control circuitry, a first annular member, and a second annular member. The control circuitry is in communication with the second motor and configured to sense a change in a condition of the second motor. The first annular member has a surface feature projecting therefrom. The second annular member is disposed adjacent the first annular member. The second annular member has a first surface feature projecting therefrom circumferentially aligned with the surface feature of the first annular member such that upon a threshold amount of rotation of the first annular member, the surface feature of the first annular member abuts the first surface feature of the second annular member to change the condition of the second motor.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein.

DETAILED DESCRIPTION

Figure 1:
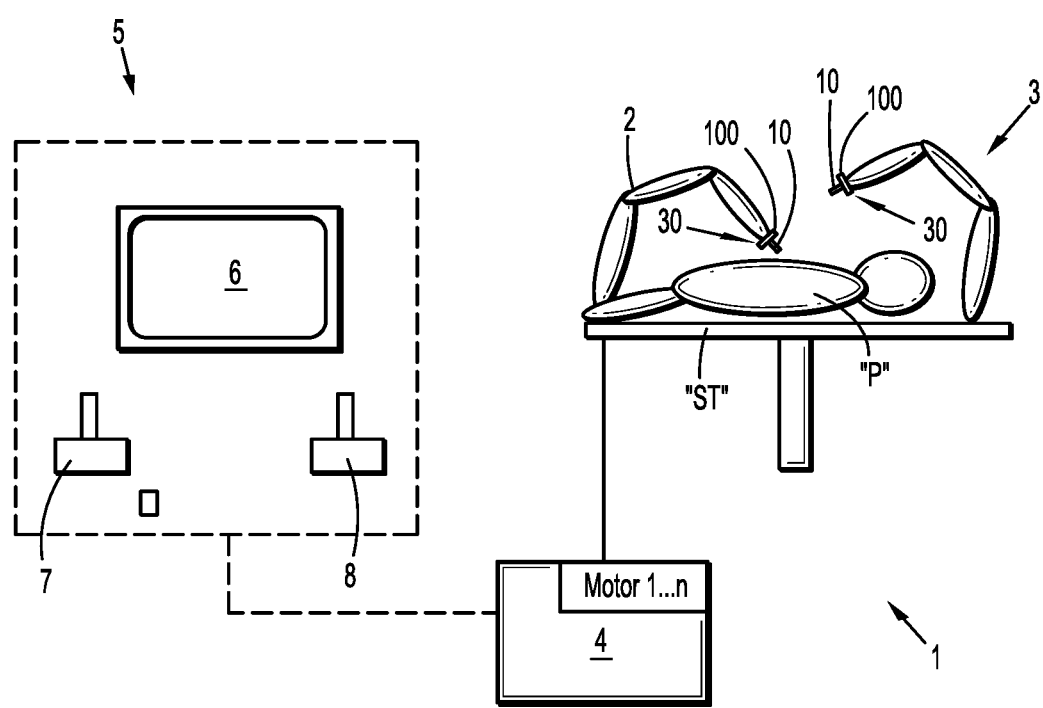
FIG. 1 is a schematic illustration of a robotic surgical system including a surgical assembly in accordance with the present disclosure.

Embodiments of the presently disclosed surgical assembly including an instrument drive unit for driving the operation of an electromechanical instrument and methods thereof are described in detail with reference to the drawings, in which like reference numerals designate identical or corresponding elements in each of the several views. As used herein the term "distal" refers to that portion of the robotic surgical system, surgical assembly, or component thereof, that is further from the user, while the term "proximal" refers to that portion of the robotic surgical system, surgical assembly, or component thereof, that is closer to the user.

As will be described in detail below, provided is a surgical assembly configured to be attached to a surgical robotic arm. The surgical assembly includes an instrument drive unit having a hollow core motor configured to rotate an electromechanical instrument about a longitudinal axis thereof. Additionally, provided is a feedback assembly configured to determine and regulate the degree of rotation of the electromechanical instrument about its longitudinal axis.

Figure 2:
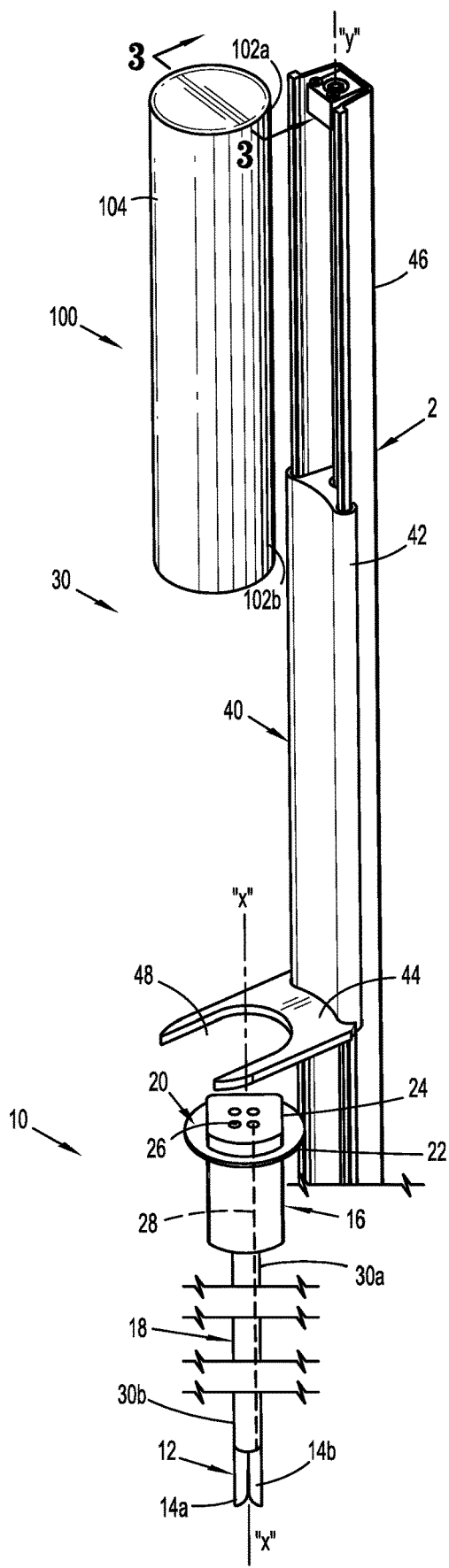
FIG. 2 is a perspective view of the surgical assembly of FIG. 1 including a slider attached to the surgical robotic arm, and an instrument drive unit separated from an electromechanical instrument.

Referring initially to FIGS. 1 and 2, a surgical system, such as, for example, a robotic surgical system 1, generally includes a plurality of surgical robotic arms 2, 3 having an instrument drive unit 100 and an electromechanical instrument 10 removably attached thereto; a control device 4; and an operating console 5 coupled with control device 4.

Operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art. Each of the robotic arms 2, 3 may be composed of a plurality of members, which are connected through joints. Robotic arms 2, 3 may be driven by electric drives (not shown) that are connected to control device 4. Control device 4 (e.g., a computer) is set up to activate the drives, in particular by means of a computer program, in such a way that robotic arms 2, 3, the attached instrument drive units 20, and thus electromechanical instrument 10 (including electromechanical end effector 12) execute a desired movement according to a movement defined by means of manual input devices 7, 8. Control device 4 may also be set up in such a way that it regulates the movement of robotic arms 2, 3 and/or of the drives.

Robotic surgical system 1 is configured for use on a patient "P" lying on a surgical table "ST" to be treated in a minimally invasive manner by means of a surgical instrument, e.g., electromechanical instrument 10. Robotic surgical system 1 may also include more than two robotic arms 2, 3, the additional robotic arms likewise being connected to control device 4 and being telemanipulatable by means of operating console 5. A surgical instrument, for example, electromechanical surgical instrument 10 (including electromechanical end effector 12, FIG. 2), may also be attached to the additional robotic arm.

Control device 4 may control a plurality of motors, e.g., motors (Motor 1 . . . n), with each motor configured to drive movement of robotic arms 2, 3 in a plurality of directions. Further, control device 4 may control a plurality of first motors M1-M4 (FIG. 3) disposed within instrument drive unit 100 that drive various operations of end effector 12 (FIG. 2) of electromechanical instrument 10, and a second motor, such as, for example, a hollow core motor (FIGS. 3 and 4), configured to drive a relative rotation of electromechanical instrument 10 along a longitudinal axis "X" thereof, as will be described in detail below. In embodiments, each motor can be configured to actuate a drive rod or a lever arm to effect operation and/or movement of each electromechanical end effector 12 of electromechanical instrument 10. In some embodiments, rather than second motor being a hollow core motor, second motor is instead a motor that operably couples to a side of instrument drive unit 100 to rotate instrument drive unit about longitudinal axis "X," such as, for example, a canister motor or the like.

For a detailed discussion of the construction and operation of a robotic surgical system, reference may be made to U.S. Pat. No. 8,828,023, filed on Nov. 3, 2011, the entire contents of which are incorporated by reference herein.

With continued reference to FIGS. 1 and 2, robotic surgical system 1 includes a surgical assembly 30, which includes the instrument drive unit 100 coupled with or to robotic arm 2, and the electromechanical instrument 10 coupled to instrument drive unit 100. Instrument drive unit 100 transfers power and actuation forces from its motors to driven members of electromechanical instrument 10 to ultimately drive movement of components of end effector 12 of electromechanical instrument 10, for example, a movement of a knife blade (not shown) and/or a closing and opening of jaw members 14a, 14b of end effector 12.

With reference to FIG. 2, electromechanical instrument 10 generally includes a housing portion 16 and a shaft 18 extending distally from housing portion 16. Housing portion 16 has a cylindrical configuration and includes a proximal end and a distal end defining a longitudinal axis "X" therebetween. The proximal end of housing portion 16 defines a male mating feature 20 configured to non-rotatably engage with a female mating feature 140 (FIG. 3) of instrument drive unit 100, as will be described in detail below. Male mating feature 20 includes a disc-shaped member 22 and a projection 24 extending proximally from disc-shaped member or flange 22. Projection 24 may be non-circular to non-rotatably couple to the correspondingly shaped female mating part 140 of instrument drive unit 100. In some embodiments, the proximal end of housing portion 16 may be non-rotatably attached to instrument drive unit 100 via various fastening engagements, such as, for example, threaded engagement, clips, latches, friction fit engagement, buttons, a variety of fasteners, and/or a bayonet-type connection.

The proximal end of housing portion 16 further includes a plurality of input drive couplers 26. Input drive couplers 26 are configured to drivingly connect to respective motors M1-M4 (FIGS. 3 and 5) of instrument drive unit 100. Input drive couplers 26 are in the form of non-circular depressions or in the form of a crown-gear defined in the projection 24 of the male mating feature 20 of housing portion 16. Input drive couplers 26 are configured for non-rotatable receipt of a correspondingly shaped drive sleeve or projection (not shown) extending from each motor M1-M4. Housing portion 16 includes driven or force transmission members 28 that extend distally from respective input drive couplers 26. As such, rotation of the drive sleeves (not shown) of the motors M1-M4 of instrument drive unit 100, via actuation of respective motors M1-M4, rotates respective input drive couplers 26 to effect rotation or translation of respective driven or force transmission members 28 of electromechanical instrument 10. In embodiments, force transmission members 28 may be configured to convert rotational forces generated by motors M1-M4 into translational forces to actuate end effector 12.

With continued reference to FIG. 2, shaft 18 of electromechanical instrument 10 has a proximal end 30a supported by housing portion 16 and a distal end 30b having end effector 12. Driven members 28 extend from housing portion 16 and through shaft 18 of electromechanical instrument 10 to operably couple to various components of end effector 12 such that rotation and/or axial movement of each driven member 28 effects actuation of various functions of end effector 12. End effector 12 generally includes a pair of opposing jaw members 14a, 14b. End effector 12 may be moved, by actuation of driven members 28, from an open configuration wherein tissue (not shown) is received between jaw members 14a, 14b, and a closed configuration, wherein the tissue is clamped and treated. In embodiments, opposing jaw members 14a, 14b may be electrically coupled to a cable, and to a generator (not shown), via respective suitable electrical wiring 122 (FIG. 3) extending through shaft 18 of electromechanical instrument 10 and through instrument drive unit 100 to provide an electrical pathway to a pair of electrically conductive, tissue-engaging sealing plates (not shown) disposed on the opposing jaw members 14a, 14b.

With continued reference to FIG. 2, surgical assembly 30 is supported on or connected to a slider 40 having a first portion 42 and a second portion 44. First portion 42 of slider 40 is movably connected to a track or slide 46 of robotic arm 2, and second portion 44 of slider 40 defines an opening 48 therethrough configured for frictional receipt of or connection with instrument drive unit 100. Slider 40 moves, slides, or translates along a longitudinal axis "Y" defined by track 46 of surgical robotic arm 2 upon a selective actuation by motor(s) (not shown) disposed in track 46 of surgical robotic arm 2 or motors (1 . . . n) of control device 4. As such, slider 40, with instrument drive unit 100 connected thereto, can be moved to a selected position along track 46 of surgical robotic arm 2.

Figure 3:
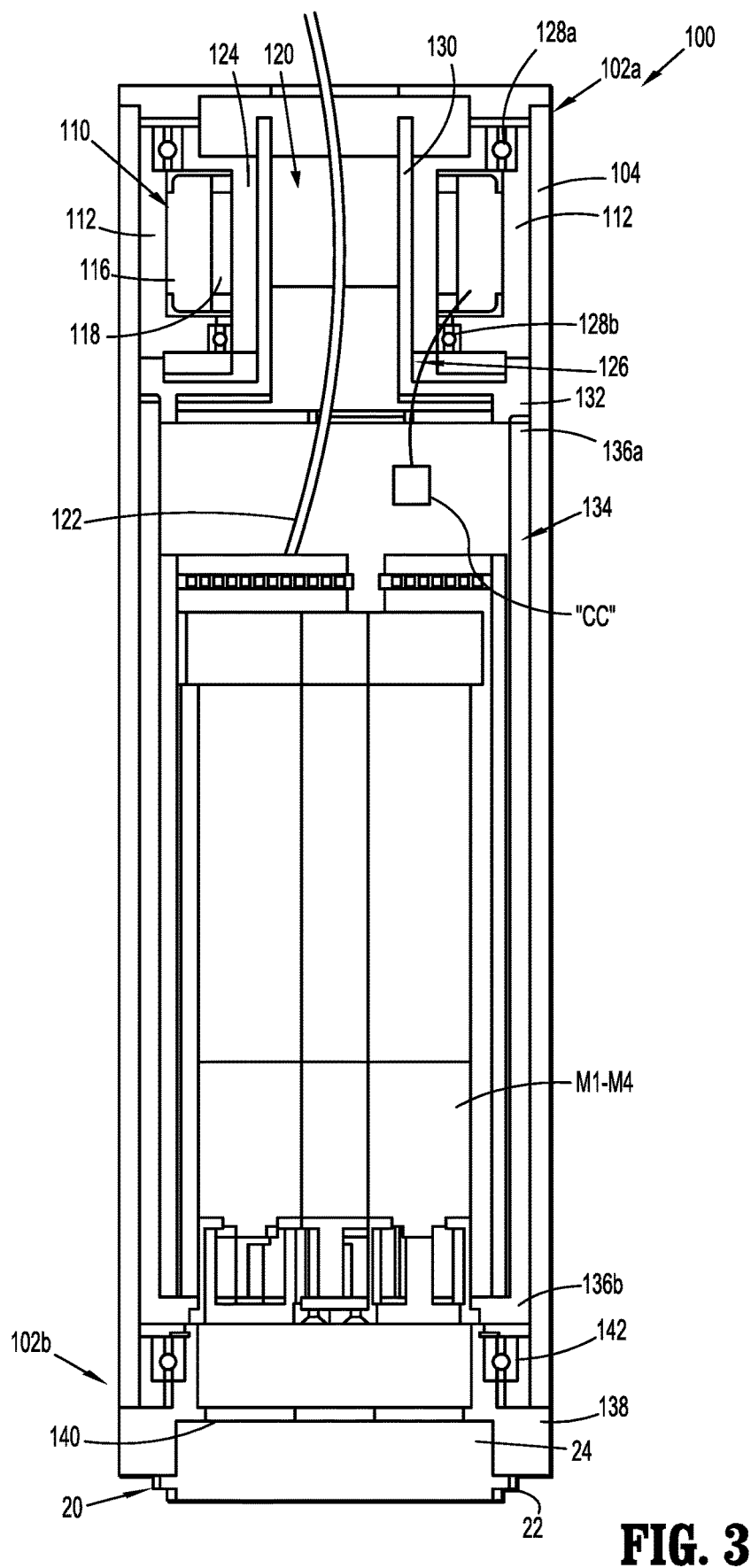
FIG. 3 is a cross-section, taken along line 3-3 in FIG. 2, of the instrument drive unit illustrating parts of a hollow core motor.
Figure 4:
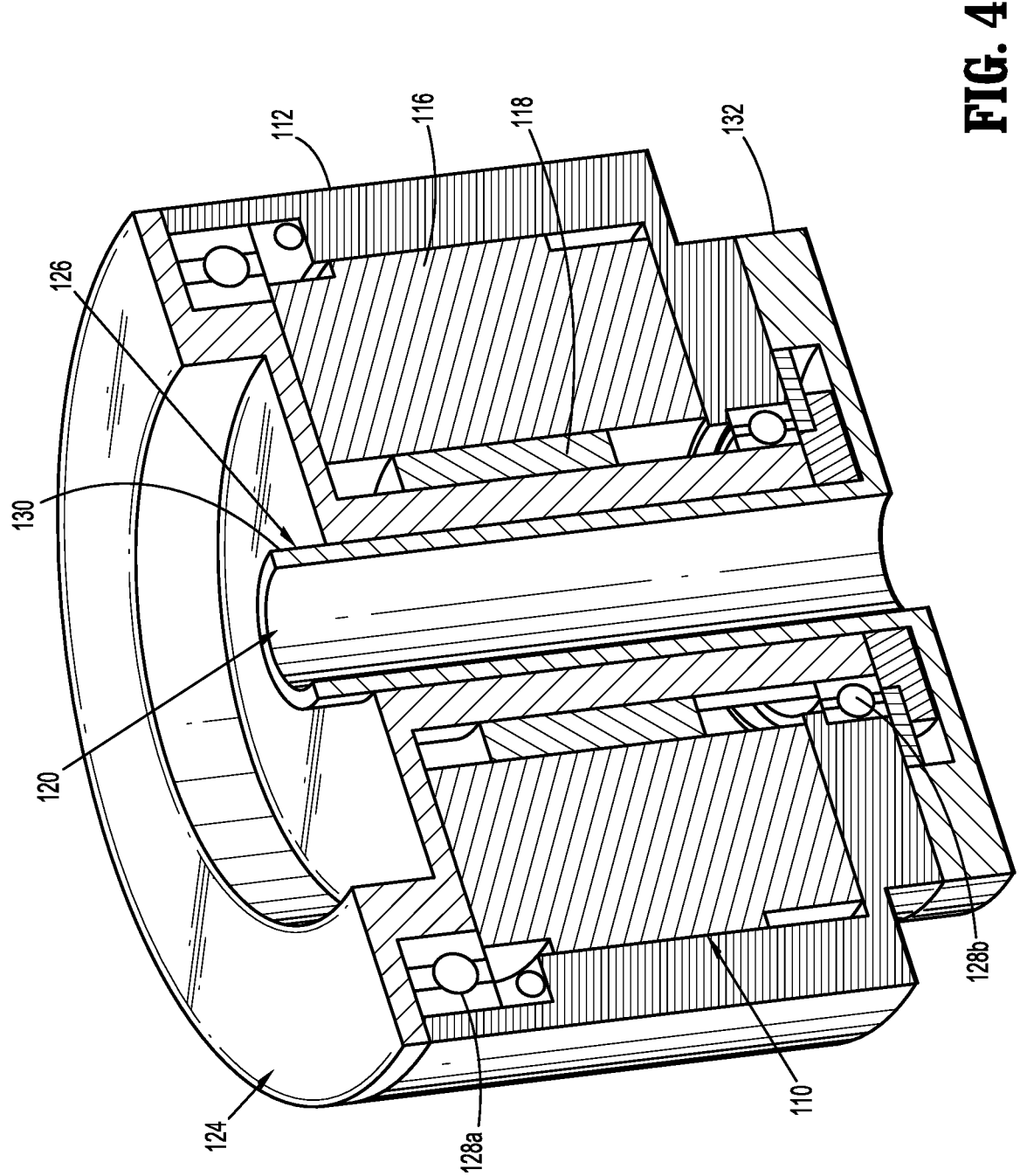
FIG. 4 is an enlarged view, with parts removed, of the instrument drive unit of FIG. 3 illustrating components of the hollow core motor and an inner hub.
Figure 5:
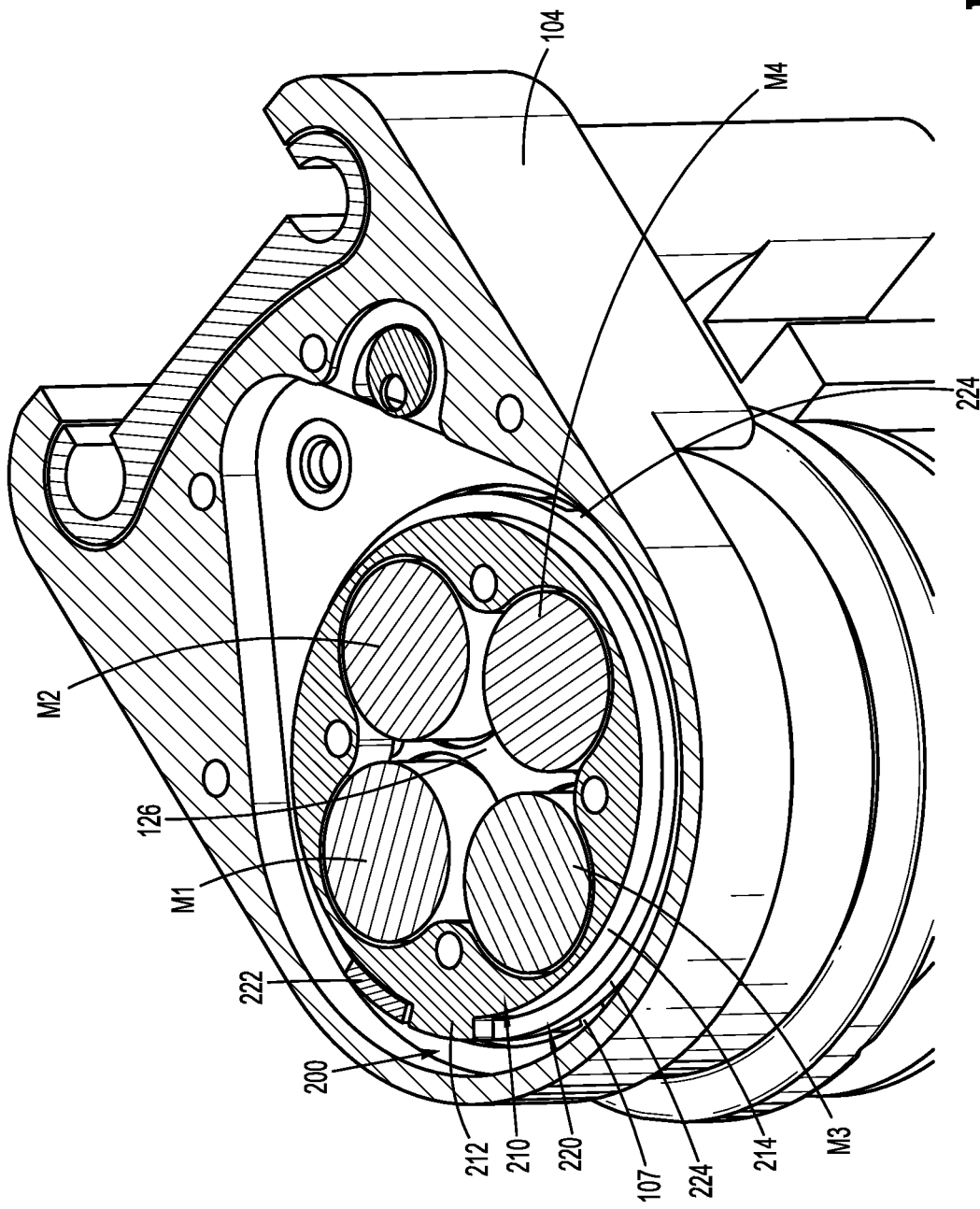
FIG. 5 is a top, cross sectional view of components of a feedback assembly of the instrument drive unit of FIG. 2.

With reference to FIGS. 2-4, instrument drive unit 100 of surgical assembly 30 has a proximal end 102a and a distal end 102b configured to be operably coupled to electromechanical instrument 10 to actuate functions of end effector 12 of electromechanical instrument 10 and to rotate electromechanical instrument 10 about its longitudinal axis "X." Instrument drive unit 100 may generally include an outer shell 104, a hollow core motor 110, and a plurality of motors M1-M4 (FIGS. 3 and 5). Outer shell 104 encloses the inner components of instrument drive unit 100 to form a sterile barrier between an interior of instrument drive unit 100 and the external environment. Outer shell 104 may be disposable, re-usable (upon sterilization), and/or transparent.

With reference to FIGS. 3 and 4, instrument drive unit 100 includes a proximal inner shell 112 fixedly engaged to an inner surface of outer shell 104 or non-rotatably disposed in an interior of outer shell 104. Hollow core motor 110 is disposed within proximal end 102a of instrument drive unit 100 and includes an outer stator 116 and an inner rotor 118. Outer stator 116 has a cylindrical configuration and is fixedly coupled to proximal inner shell 112, such that outer stator 116 is non-rotatable relative to outer shell 104. Inner rotor 118 has a cylindrical configuration and is rotatably, coaxially disposed within outer stator 116. Inner rotor 118 has a generally tube-like configuration having an inner surface that defines a longitudinal central channel 120 of inner rotor 118. Longitudinal central channel 120 of inner rotor 118 permits passage of an electrical wire 122 extending therethrough for providing electrical energy or power from a power source (e.g., a generator) to one of the plurality of motors M1-M4. In some embodiments, a plurality of electrical wires extend through longitudinal central channel 120 of hollow core motor 110 to provide power to each of motors M1-M4 and/or components of end effector 12.

Instrument drive unit 100 includes outer and inner hubs 124, 126 coaxially disposed within longitudinal channel 120 of inner rotor 118 of hollow core motor 110. Outer hub 124 is frictionally retained or keyed between inner rotor 118 of hollow core motor 110 and inner hub 126 such that outer hub 124 transmits rotational movement of inner rotor 118 to inner hub 126. Proximal end 102a of instrument drive unit 100 includes first and second proximal bearings 128a, 128b each disposed between outer hub 124 and proximal inner shell 112 to facilitate rotation of outer hub 124 relative to proximal inner shell 112.

Inner hub 126 has a cylindrical portion 130 and a base flange 132. Cylindrical portion 130 of inner hub 126 is disposed within outer hub 124 and rotatable therewith. Instrument drive unit 100 further includes a distal inner shell 134 (FIG. 3), which has the plurality of motors M1-M4 supported therein. Base flange 132 of inner hub 126 is connected to and is contiguous with a proximal end 136a of distal inner shell 134 such that rotational movement of inner hub 126 causes rotational movement of distal inner shell 134.

Distal inner shell 134, unlike proximal inner shell 112, is rotatable within and relative to outer shell 104. Distal inner shell 134 has a distal end 136b configured to be non-rotatably coupled to the proximal end of electromechanical instrument 10 such that distal inner shell 134 transmits rotational movement of inner hub 126 to electromechanical instrument 10. In particular, distal end 102b of instrument drive unit 100 includes a distal cap 138 that extends distally from distal end 136b of distal inner shell 134. Distal cap 138 defines female mating feature 140 of instrument drive unit 100, which is configured to matingly receive male mating feature 20 of housing portion 16 of electromechanical instrument 10, as mentioned above. Distal end 102b of instrument drive unit 100 further includes a distal bearing 142 disposed between distal cap 138 and outer shell 104 to facilitate rotation of distal inner shell 134 and distal cap 138 relative to outer shell 104.

To assemble surgical assembly 30, instrument drive unit 100 is positioned within opening 48 defined in slider 40 to non-rotatably couple instrument drive unit 100 to surgical robotic arm 2. Male mating feature 20 of housing portion 16 of electromechanical instrument 100 is matingly engaged to female mating part 140 of instrument drive unit 100. Upon coupling instrument drive unit 100 and electromechanical instrument 10 to one another, projection 24 of male mating feature 20 of electromechanical instrument 10 non-rotatably couples to distal cap 138 of instrument drive unit 100, and input drive couplers 26 of electromechanical instrument 10 operably engage drive sleeves (not shown) extending from respective motors M1-M4 of instrument drive unit 100.

In use, to rotate electromechanical instrument 10 about longitudinal axis "X" thereof, a current is transmitted to hollow core motor 110 via a power supply (not shown). As hollow core motor 110 receives current, inner rotor 118 of hollow core motor 110 is caused to rotate relative to outer stator 116 of hollow core motor 110 and outer shell 104 of instrument drive unit 100. Rotation of inner rotor 118 of hollow core motor 110 rotates outer hub 124, which causes inner hub 126 to rotate due to cylindrical portion 130 of inner hub 126 being frictionally retained within outer hub 124. Base flange 132 of inner hub 126 is non-rotatably connected to proximal end 136a of distal inner shell 134 such that rotation of inner hub 126 effects rotation of distal inner shell 134. Rotation of distal inner shell 134 causes distal cap 138 to rotate therewith. Rotation of distal cap 138 of instrument drive unit 100 relative to outer shell 104 effects rotation of electromechanical instrument 10 about longitudinal axis "X" thereof due to distal cap 138 being non-rotatably connected to housing portion 16 of electromechanical instrument 10. As such, electromechanical instrument 10 may be selectively rotated about its longitudinal axis "X" to a desired rotational position upon actuation of hollow core motor 110.

With reference to FIG. 5, an embodiment of a feedback assembly 200 is provided. Feedback assembly 200 is configured to determine and indicate the degree to which electromechanical instrument 10 rotates about longitudinal axis "X," as will be described in detail below. It is contemplated that feedback assembly 200 may be configured to calculate/determine and display the amount of revolution(s) of electromechanical instrument 10, relative to instrument drive unit 100 and slider 44 about longitudinal axis "X," so that a clinician can determine the precise rotational position of electromechanical instrument 10 during use thereof.

Feedback assembly 200 is incorporated into or associated with control circuitry "CC" (FIG. 3) of the second motor 110 of instrument drive unit 100. Feedback assembly 200 of surgical assembly 30 includes a first annular member 210 stacked on a second annular member 220. Annular members 210, 220 each have a disc-shaped configuration and each define central bores having the plurality of first motors M1-M4 disposed therethrough. First annular member 210 is disposed concentrically within or adjacent second annular member 220 and is non-rotatably coupled to inner hub 126 of instrument drive unit 100 such that rotation of inner hub 126 results in concomitant rotation of first annular member 210. In some embodiments, first annular member 210 may be integrally formed with inner hub 126 or distal cap 138 (FIG. 3). First annular member 210 has a surface feature or tab 212 projecting radially from a circumferential edge 214 thereof. Surface feature 212 may have a squared configuration. In some embodiments, surface feature 212 may assume a variety of shapes, such as, for example, triangular, arcuate, polygonal, uniform, non-uniform, tapered, or the like.

Second annular member 220 may surround inner hub 126, or may be disposed adjacent (e.g., distal) inner hub 126, and is rotatable relative to inner hub 126. Second annular member 220 has a first surface feature or tab 222 projecting proximally from a circumferential edge 224 thereof. First surface feature 222 of second annular member 220 is circumferentially aligned (i.e., cocircumferential) with surface feature 212 of first annular member 210 and is circumferentially or radially spaced from surface feature 212 of first annular member 220 by a selected amount. For example, in the illustrative embodiment of FIG. 5, first surface feature 222 of second annular member 220 is circumferentially spaced, in a clockwise direction, from surface feature 212 of first annular member 210 by about 360°. As such, upon a threshold amount of rotation (e.g., 360° in a counter-clockwise direction) of first annular member 210, surface feature 212 of first annular member 210 abuts or engages first surface feature 222 of second annular member 220.

In some embodiments, surface feature 212 of first annular member 210, instead of being integrally formed with first annular member 210, may be resiliently biased from first annular member 210 toward a radially outward position, and first surface feature 222 of annular member 220 may have a depression formed therein. As such, upon surface feature 212 of first annular member 210 being rotated into radial alignment with the depression (not shown) formed in second surface feature 222 of second annular member 220, surface feature 212 of first annular member 210 biases radially outwardly into engagement with the correspondingly shaped depression (not shown) formed in second annular member 220. Upon receipt of surface feature 212 of first annular member 210 in the depression formed in second annular member 220, first annular member 210 clutches second annular member 220 such that second annular member 220 rotates with first annular member 210.

Second annular member 220 has a second surface feature 224 projecting distally from circumferential edge 224 thereof. Second surface feature 224 is circumferentially spaced from first surface feature 222 by about 180°. In some embodiments, second surface feature 224 may be circumferentially spaced from first surface feature 222 by a variety of distances, such as, for example, between about 1° and about 360°, or may be radially aligned with first surface feature 222. Outer shell 104 has a surface feature or tab 107 extending inwardly therefrom such that upon the second annular member 220 achieving a threshold amount of rotation relative to outer shell 104, second surface feature 224 of second annular member 220 abuts or engages surface feature 107 of outer shell 104 of instrument drive unit 100 to stop rotation of inner hub 126, which stops rotation of electromechanical instrument 10 about its longitudinal axis "X."

It is contemplated, in accordance with an embodiment of the present disclosure, feedback assembly 200 incorporates a highly toleranced resistor "R" (not shown) with an extremely low resistance, about 0.05 ohms, that is added to a low side of an H-bridge responsible for driving second motor 110. In operation, feedback assembly 200 measures a voltage "V" across resistor "R." By measuring the voltage "V" drop across resistor "R," the feedback assembly 200 may calculate an amount of current "I" flowing through resistor "R" using Ohm's Law:

$$V=IR$$

In a DC electric motor, which second motor 110 may be constructed as, current "I" is directly related to the amount of torque "τ" being developed by using a relation, e.g., the Torque Constant ($K_m$). Accordingly, the feedback assembly 200 can calculate the amount of torque "τ" being applied to second motor 110 according to the following equation:

$$\tau=(Km)(I)$$

Reference may be made to U.S. Pat. No. 8,517,241, filed on Mar. 3, 2011, for a detailed description of an exemplary embodiment of a feedback assembly configured to calculate an amount of torque being applied to motors, the entire contents of which are incorporated by reference herein.

During a normal rotation of electromechanical instrument 10, a certain or predetermined force profile is expected to be seen by feedback assembly 200 in control circuitry "CC" of electromechanical instrument 10, e.g., either a current v. time profile (not shown) or a current v. distance profile (not shown). In use, an actuation of second motor 110 effects a rotation of inner hub 126 of instrument drive unit 100 as described above. A rotation of inner hub 126 rotates first annular member 210, via their non-rotatable connection, to ultimately place surface feature 212 of first annular member 210 into engagement with first surface feature 222 of second annular member 220. Upon surface feature 212 of first annular member 210 engaging or coming into contact with first surface feature 222 of second annular member 220, the static inertia of second annular member 220 must be overcome by a certain threshold amount of added torque provided by second motor 110. The additional torque required to begin rotating second annular member 220 changes a condition of second motor 110, which is a change in current "I" delivered to second motor 110, which is a different amount of current compared to the expected force profile stored in control circuitry "CC."

This increase in current "I" or current spike is registered by control circuitry "CC," and control circuitry "CC" can reasonably assume that electromechanical instrument 10 has rotated a threshold amount from its original position. In particular, the current spike indicates that first annular member 210 has rotated a predetermined threshold amount (e.g., 360°) from its original rotational position. Since first annular member 210 rotates with electromechanical instrument 10, the threshold amount of rotation of first annular member 210 registered by control circuitry "CC" correlates to the same threshold amount of rotation traveled by electromechanical instrument 10 about its longitudinal axis "X."

As mentioned above, display 6 (FIG. 1) may be provided to indicate, in the form of a number of degrees, the determined amount of rotation of electromechanical instrument 10.

Continued rotation of electromechanical instrument 10 eventually causes second surface feature 224 of second annular member 220 to abut or engage surface feature 107 of outer shell 104, which results in another current spike and an instruction to cease delivering current to second motor 110, thereby ceasing rotation of second annular member 220, and therefore electromechanical instrument 10. It is envisioned that surface feature 107 of outer shell 104 may resist or prevent further rotation of second annular member 220 due to surface feature 224 of annular member 220 mechanically engaging surface feature 107 of outer shell 104.

Figure 6:
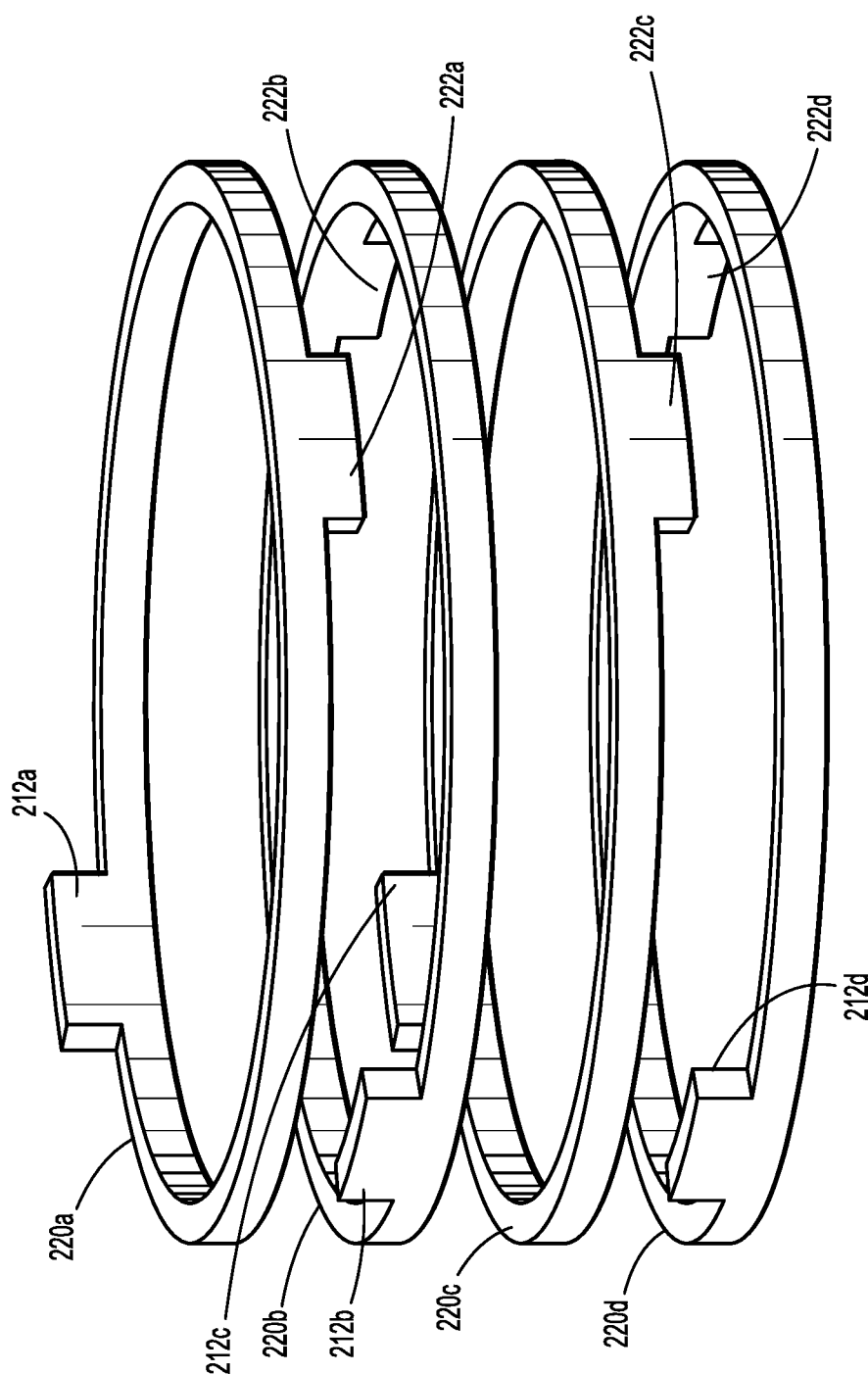
FIG. 6 is a perspective view of another embodiment of the feedback assembly of FIG. 5 including four stackable annular members.

In some embodiments, feedback assembly 200 may include a single annular member or more than two annular members having any suitable number of variously spaced surface features or tabs. For example, with reference to FIG. 6, feedback assembly 200 may include four annular members 220a, 220b, 220c, 220d stacked upon one another. In this example, each of the four stacked annular members 220a, 220b, 220c, 220d may have a first surface feature or tab 212a, 212b, 212c, 212d, respectively, similar to surface features 212, 222, or 224 mentioned above, extending upwardly therefrom, and a second surface feature or tab 222a, 222b, 222c, 222d, respectively, extending downwardly therefrom. The first tab 212a, 212b, 212c, 212d of each annular member 220a, 220b, 220c, 220d is circumferentially spaced from the second tab 222a, 222b, 222c, 222d of each respective annular member 220a, 220b, 220c, 220d by 180°.

As such, after an initial 180° rotation of inner hub 126, which is associated with firs tab 212 of first annular member 220a, first annular member 220a will begin to rotate. After first annular member 220a rotates 180°, the second tab 222a of first annular member 220 engages first tab 212b of adjacent, second annular member 220b to effect rotation of second annular member 220b. An additional 180° rotation of inner hub 126 will position second tab 222b of second annular member 220b into engagement with first tab 212c of third annular member 220c causing third annular member 220c to begin to rotate, etc. In this way, every 180° rotation of inner hub 126 will be registered by control circuitry "CC," due to respective current spikes in the operation of second motor 110, which can ultimately be indicated on display 6 so a clinician can identify the rotational position of electromechanical instrument 10 in 180° increments. As can be understood, the more annular members making up feedback assembly 200, the more precisely the rotational position of electromechanical instrument 10 can be identified.

It is contemplated that upon fourth annular member 220d completing its rotation, second tab 222d of fourth annular member 220 abuts surface feature 107 (FIG. 5) of outer shell 104 of instrument drive unit 100. Upon second tab 222d of fourth annular member 220 abutting surface feature 107 of outer shell 104 of instrument drive unit 100, control circuitry "CC" (FIG. 3) stops the delivery of current to second motor "M2." As such, rotation of inner hub 126 is stopped, which stops rotation of electromechanical instrument 10 (FIG. 2) about its longitudinal axis "X." It can be appreciated that the amount that electromechanical instrument 10 is capable of rotating is directly correlated to the number of annular members being used (i.e., the greater the number of annular members that are stacked upon one another, the more electromechanical instrument 10 will be able to rotate before it is stopped).

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. An instrument drive unit for use with a robotic surgical system, the instrument drive unit comprising:
 a motor configured to effect rotation of a surgical instrument; and
 a feedback assembly including:
  a first annular member having a surface feature, the first annular member configured to rotate in response to an activation of the motor;
  a second annular member disposed adjacent the first annular member, the second annular member having a first surface feature located such that the surface feature of the first annular member engages the first surface feature of the second annular member upon a threshold amount of rotation of the first annular member; and
  control circuitry configured to determine an amount the surgical instrument rotates based on the surface feature of the first annular member engaging the first surface feature of the second annular member.

2. The instrument drive unit according to claim 1, wherein the control circuitry is in communication with the motor and configured to sense a change in a condition of the second motor, the condition of the second motor changing in response to the surface feature of the first annular member engaging the first surface feature of the second annular member.

3. The instrument drive unit according to claim 2, wherein the change in condition of the motor is a change in current delivered to the motor upon the engagement of the surface feature of the first annular member and the first surface feature of the second annular member.

4. The instrument drive unit according to claim 1, wherein the first surface feature of the second annular member is a projection, and the surface feature of the first annular member is a projection.

5. The instrument drive unit according to claim 1, wherein the first surface feature of the second annular member is a projection or a depression, and the surface feature of the first annular member is the other of a projection or a depression.

6. The instrument drive unit according to claim 1, wherein the surface feature of the first annular member is movable along an annular path, and the first surface feature of the second annular member is disposed adjacent or on the annular path of the surface feature of the first annular member.

7. The instrument drive unit according to claim 1, wherein the surface feature of the first annular member is circumferentially aligned with the first surface feature of the second annular member.

8. The instrument drive unit according to claim 1, wherein the first and second annular members are stacked relative to one another.

9. The instrument drive unit according to claim 1, wherein the first and second annular members are concentrically disposed with one another.

10. The instrument drive unit according to claim 1, wherein the second annular member has a second surface feature projecting therefrom, circumferentially spaced from the first surface feature, the instrument drive unit further comprising an outer shell having a surface feature extending inwardly therefrom such that upon the second annular member achieving a threshold amount of rotation relative to the outer shell, the second surface feature of the second annular member abuts the surface feature of the outer shell to stop rotation of the surgical instrument.

11. The instrument drive unit according to claim 1, further comprising:
 an outer shell configured to be coupled to a robotic arm; and
 an inner hub rotatably disposed within the outer shell and configured to be non-rotatably coupled to the surgical instrument.

12. The instrument drive unit according to claim 11, wherein the motor includes:
 an outer stator fixedly coupled to the outer shell; and
 an inner rotor rotatably disposed within the outer stator, the inner rotor having an inner surface that defines a longitudinal channel having the inner hub non-rotatably disposed therein, wherein activation of the motor rotates the inner hub to effect rotation of the surgical instrument.

13. The instrument drive unit according to claim 12, further comprising an outer hub disposed between the inner rotor and the inner hub such that the outer hub transmits rotational movement of the inner rotor to the inner hub.

14. The instrument drive unit according to claim 13, further comprising an inner shell rotatably disposed within the outer shell and having a proximal end coupled to the inner hub and a distal end configured to be coupled to a proximal end of the surgical instrument such that the inner shell transmits rotational movement of the inner hub to the surgical instrument.

15. The instrument drive unit according to claim 1, wherein the first and second annular members are disposed about the motor.

16. A surgical assembly for use with and for selective connection to a robotic arm, the surgical assembly comprising:
 a surgical instrument including a driven member; and
 an instrument drive unit including:
  a first motor configured to be operably coupled to the driven member of the surgical instrument;
  a second motor configured to be coupled to the surgical instrument to effect rotation of the surgical instrument; and
  a feedback assembly including:
   control circuitry in communication with the second motor and configured to sense a change in a condition of the second motor;
   a first annular member having a surface feature configured to move along an annular path; and
   a second annular member disposed adjacent the first annular member, the second annular member having a first surface feature disposed adjacent or on the annular path such that upon a threshold amount of rotation of the first annular member, the surface feature of the first annular member engages the first surface feature of the second annular member to change the condition of the second motor.

17. The surgical assembly according to claim 16, wherein the first surface feature of the second annular member is a projection, and the surface feature of the first annular member is a projection.

18. The surgical assembly according to claim 16, wherein the first surface feature of the second annular member is a projection or a depression, and the surface feature of the first annular member is the other of a projection or a depression.

19. The surgical assembly according to claim 16, wherein the surface feature of the first annular member is circumferentially aligned with the first surface feature of the second annular member.

20. The surgical assembly according to claim 16, wherein the first and second annular members are at least one of stacked relative to one another or concentrically disposed with one another.

\* \* \* \* \*